United States Patent [19]

Sloane, Jr. et al.

[11] Patent Number: 5,047,211
[45] Date of Patent: Sep. 10, 1991

[54] DISPOSABLE BLOOD HANDLING CASSETTE DEVICE FOR MEASURING HAEMOSTASIS

[75] Inventors: Thomas E. Sloane, Jr., West Redding; Joseph W. Blake, III, Norwalk, both of Conn.

[73] Assignee: Xylum Corporation, Scarsdale, N.Y.

[21] Appl. No.: 395,843

[22] Filed: Aug. 18, 1989

[51] Int. Cl.⁵ .................. G01N 11/04; G01N 11/08; G01N 33/49
[52] U.S. Cl. ........................ 422/73; 73/64.1; 128/638; 422/82.13; 436/69; 436/70
[58] Field of Search .............. 422/73, 82.13, 68.1, 422/100, 103; 436/69, 70; 73/64.1; 128/638, 672

[56] References Cited

U.S. PATENT DOCUMENTS 4,797,369 1/1989 Mintz ........................ 422/73 X

FOREIGN PATENT DOCUMENTS 0129425 12/1984 European Pat. Off. .
8700633 1/1987 PCT Int'l Appl. .
8802116 3/1988 PCT Int'l Appl. .

Primary Examiner—Jill Johnston
Attorney, Agent, or Firm—Pollock, Vande Sande & Priddy

[57] ABSTRACT

A disposable blood holding cassette for haemostatic measurements. A single unit is provided having a blood sample container with three separate pressurized blood sample reservoirs. A waste blood collection reservoir is connected to the blood sample container, and connected thereto via first, second and third blood sample tubes. A punching station is provided to accurately punch first and second of the blood sample tubes, simulating haemostasis function in vitro. Measurements may be made of the haemostatic and thrombolytic function of recently sampled blood. The entire device is disposable, isolating any contaminated blood from clinical personnel.

18 Claims, 5 Drawing Sheets

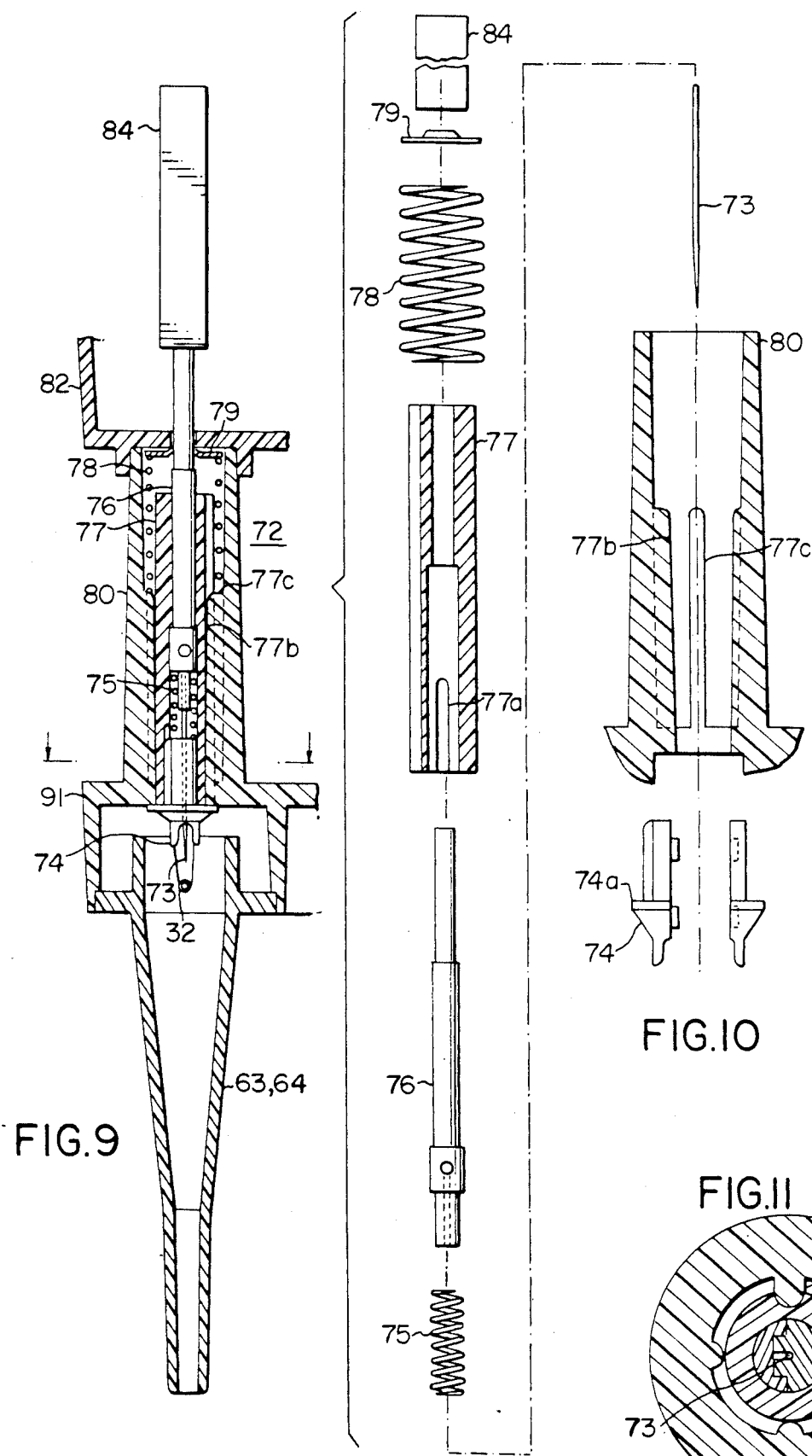

DISPOSABLE BLOOD HANDLING CASSETTE DEVICE FOR MEASURING HAEMOSTASIS

BACKGROUND OF THE INVENTION

The present invention relates to the analysis of haemostasis, clotting time, and platelet collagen interaction of non-anti-coagulated blood. Specifically, a disposable blood-handling device for making haemostasis measurements and thrombolysis measurements is described.

In the treatment of blood disorders, such as hemophilia, von Willebrand's Disease, and others, it is necessary to measure the clotting ability of human blood, and to assess the adequacy of the hemostatic function before an operation on patients having these disorders may be safely undertaken. In other disorders, such as myocardial infarction and stroke, thrombolysis or blood dissolution properties must be monitored and assessed repeatedly following recovery to prevent recurrence of a blood clot.

The haemostasis and thrombosis functions are related to the formation of platelets, red cell behavior and the condition of the vessel walls of a patient. In vitro techniques for measuring these properties have been slow in developing. One technique of in vitro analysis was described in a paper by Paul Didishen, at the Mayo Clinic, and reported in "Microscopically Typical Thrombi and Haemostatic Plug in Teflon Arteriovenus Shunts" in *Dynamics of Thrombus Formation and Dissolution*, S. A. Johnson, M. M. Guest, Eds., Lippincott, Philadelphia, USA, pages 64-71. This paper established the formation of haemostasis by passing a sample of anti-coagulated blood through a polyethylene tube which was punctured with a small hole to simulate bleeding. This effort demonstrated that haemostasis occurred at least in part from factors other than the vessel wall condition.

In building on this technique for in vitro establishment of haemostasis, European Patent Application No. 129425 describes a laboratory technique for measuring haemostasis. A polyethylene tube connected to a syringe of fresh blood is punctured with a small hole to simulate bleeding. The bleeding and clotting time of human blood samples in this arrangement can be repeatedly monitored and evaluated with and without the presence of various agents which promote haemostasis or thrombolytic activity.

In yet a further improvement of this technique, as described in International Patent Application No. PCT/GB87/00633, having an international filing date of Sept. 10, 1987, multiple channels of tubing are connected to individual syringes of freshly drawn blood. The multiple channels are simultaneously punched by a common punching needle. This permits the concurrent measurement of haemostasis and thrombolysis promoting agents on a single patient by providing two identical samples of blood, one of which may contain an agent promoting either haemostasis or thrombolysis, the other being native untreated blood.

These techniques remain impractical for operation by technicians employed in medical clinics. These clinics typically see many patients in a given day, and must have an in vitro diagnostic instrument which is easily operated and produces uniform, repeatable results. The measurements must be made quickly following drawing of a blood sample in order to obtain an accurate measurement of haemostasis. The equipment used to handle the blood samples should ideally be completely disposable to prevent the spread of disease carried by infected blood which is being tested. Additionally, it is desirable to avoid all contact with blood to prevent any disease being contracted by the laboratory personnel.

SUMMARY OF THE INVENTION

It is therefore an object of this invention to provide a clinical haemostatometer which provides reliable measurements of haemostasis of recently-taken blood samples.

It is yet a more specific object of this invention to provide a disposable cassette used in haemostasis and thrombolysis measurements to isolate infected blood samples and provide proper disposal thereof.

These and other objects of the invention are provided by a disposable blood-handling cassette which is used in haemostasis and related measurements of human blood. The cassette is used in a process which permits accurate and reliable measurement of the haemostasis function on recently-drawn blood samples. The cassette includes a blood sample container which receives a sample of blood drawn in a hypodermic syringe. The blood sample container is connected to a supply of displacing media which forces the blood through an outlet into a blood sample tube.

In the preferred embodiment of the invention, there are at least two individual blood sample containers having outlets connected by blood sample tubes to individual blood sample collection chambers. The blood sample collection chambers are connected to a supply of displacing media for forcing any air from the collection chambers to an overflow tube. The overflow tube is discharged into a collection compartment within the base of the cassette.

Individual pressure transducers monitor the pressure in the hydraulic circuit comprising a blood sample container, sample tube and collection chamber. Located along the blood sample tubes is a punching station for individually punching a pin-hole through the sample tubes. The punching station includes individual plungers which accurately align a punching needle with respect to an individual sample tube to diametrically puncture the aligned tube with a small enough hole to simulate bleeding in a human. The tubes have an inner diameter small enough to simulate a blood vessel. The exiting blood is collected in the waste collection compartment.

The precision in which the blood sample tubes are punched permits accurate and repeatable data to be taken on the blood samples. Blood samples may be simultaneously tested for the haemostasis function. This is especially useful when one of the samples includes a thrombolysis promoting agent. The thrombolytic activity of the agent for a patient can be accurately measured using these blood samples which were taken at the same time.

At the conclusion of the test, the cassette may be detached from the pressure transducers and pressurizing media and safely discarded. The tested blood is maintained completely isolated from the personnel, avoiding any possible spread of disease from infected blood.

DESCRIPTION OF THE FIGURES

FIG. 9 illustrates the punching station assembly.

FIG. 10 is an exploded view of the plunger of the punching station.

FIG. 11 is a section view of the plunger illustrating the relationship between the needle assembly and needle guide.

DESCRIPTION OF THE PREFERRED EMBODIMENT

Figure 1:
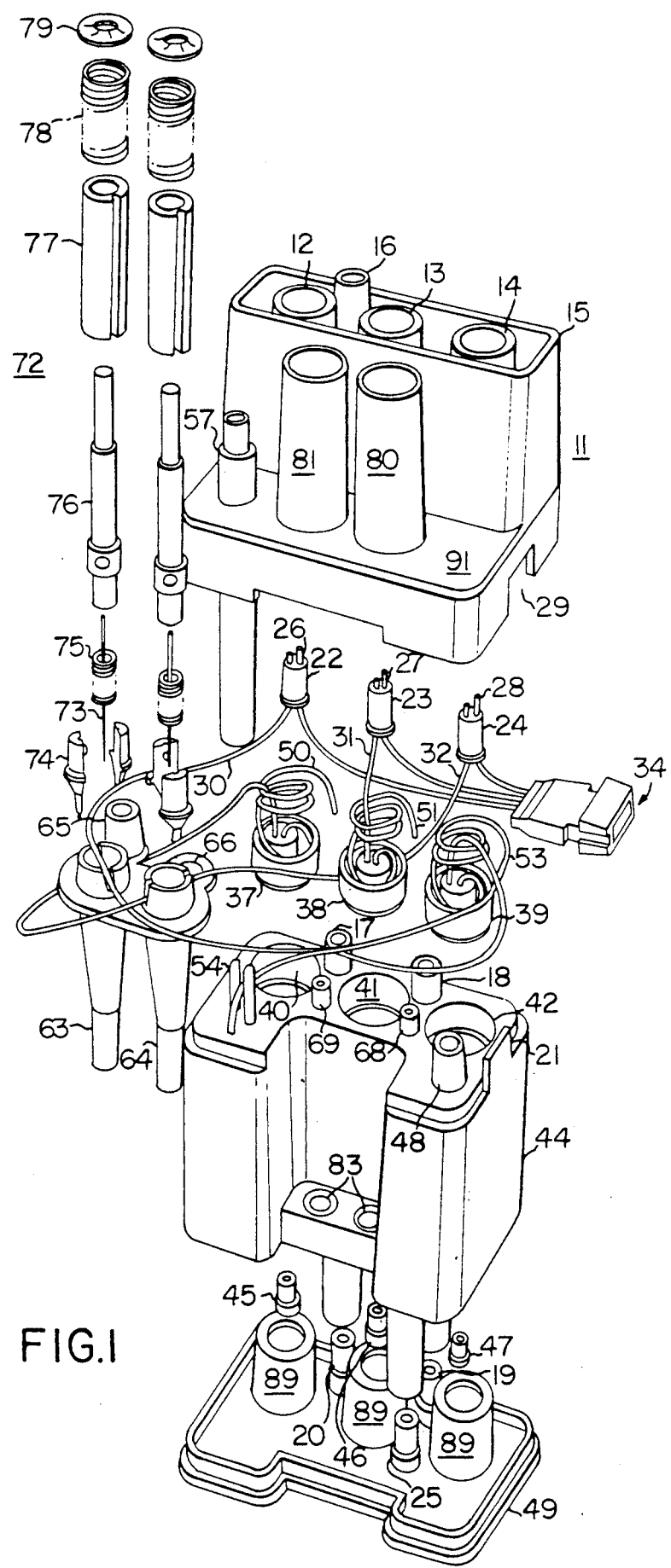
FIG. 1 is an exploded view of the major components of the blood-holding cassette in accordance with the preferred embodiment of the invention.

FIG. 1 demonstrates the major components of the blood-holding cassette, in an exploded view, used in measuring haemostasis and thrombolytic properties of blood. The device shown in FIG. 1 includes four major components. The first component is a blood supply reservoir 11. The blood supply reservoir 11 includes three separate blood sample containers 12, 13 and 14. The cap for the blood sample reservoir has been removed in this Figure, but will be demonstrated in FIGS. 2 and 3. The cap assembly includes a port for filling each of the individual containers 12, 13 and 14 with samples of blood drawn from a patient. The cap has a sealable inlet for receiving a syringe full of drawn blood, as well as a sealable vent equipped with a filter for venting the container during filling. A heating jacket 15 is shown surrounding the blood sample containers 12, 13 and 14. The heating jacket 15 is filled with a recirculated heated fluid which may be water entering port 19 and flowing through port 18 into the heating jacket 15. An overflow 16 will convey the heated water back through outlet 17 to the base 49 of the device to port 20 to be recirculated. Thus, blood samples contained in containers 12, 13 and 14 are maintained at a temperature providing for accurate in vitro measurements to be made on the blood.

Supported on a platform 91 extending from the blood supply reservoir 11 are plunger housings 80 and 81. These plunger housings will support the punching station 72 on the front of the blood cassette.

A waste receptacle 44 is shown which is connected to the blood supply reservoir 11. Cooperating tongue 21, and slot 29 captivate a connector 34. The waste receptacle 44 includes three separate blood collection chambers 40, 41 and 42. These separate blood collection chambers may be pressurized through injection sites 45, 46 and 47, inserted to the inlets of blood collection chambers 40, 41 and 42.

The area within the waste receptacle 44 between each of the blood collection chambers 40, 41 and 42 and the exterior wall of the waste receptacle 44 are used to collect discarded blood which has been tested in accordance with the operation of the device. A vent 48 is provided to vent the collecting volume through a filter.

The individual blood collection chambers 40, 41 and 42 are connected via blood sample tubes 30, 31 and 32 to the individual blood sample containers 12, 13 and 14 of the blood supply reservoir 11. Blood collection chamber caps 37, 38 and 39 seal the individual blood collection chambers 40, 41 and 42. The blood collection chamber caps each include an overflow tube 50, 51 and 53 which vent any air in the blood collection chambers into the waste receptacle 44. Once the air has vented, paraffin oil within the blood collection chambers will be displaced by pressurized blood entering the blood collection chamber. Only one of the overflow tubes, 53, is shown connected into the waste receptacle 44, but it should be understood that the remaining end of overflow tubes 50 and 51 are also connected through like openings into the waste receptacle 44. These connections were omitted for the sake of clarity in illustrating the device. The overflow tubes also provide a resistance function permitting venting of chambers 40, 41 and 42, while also maintaining a back pressure on the collection chambers 40, 41 and 42.

The blood sample tubes 30, 31 and 32 are connected to the individual blood sample containers 12, 13 and 14 through bulkhead connectors 22, 23 and 24. These bulkhead connectors additionally convey pressurizing media which may be paraffin oil through individual pressurizing tubes 26, 27 and 28. These individual tubes are connected to a captivated connector 34 which can be connected to a supply of paraffin oil for individually pressurizing each of the blood sample chambers 12, 13 and 14.

During testing of the blood for haemostasis and related properties, blood will be forced by the pressurizing media in each of the individual blood containers 12, 13 and 14 through the blood sample tubes 30, 31 and 32 into the blood collection chambers 40, 41 and 42. The blood collection chambers 40, 41 and 42 are likewise pressurized after inserting blood samples into the sample containers 12, 13 and 14 by means of paraffin oil, or another pressurizing media which enters through the injection sites 45, 46 and 47 in the base 49 of the cassette. This allows the blood collection chambers 40, 41 and 42 to be purged of air and, when blood enters the collection chambers 40, 41 and 42, the pressurizing media is displaced through the venting tubes 50, 51 and 53 into the waste receptacle 44.

Once blood samples are inserted in the blood sample containers 12, 13 and 14, and the system pressurized to a stable pressure, testing of the individual blood samples may commence. Two of the blood sample tubes, 30 and 32, pass through a punching station, generally identified as 72. The punching station, supported on the face of the waste receptacle 44 and blood supply reservoir 11, permits a hole to be accurately punched across the full diameter of each of the two blood sample tubes 30 and 32. This will provide for a haemostatic condition, wherein bleeding commences through the punched holes and primary haemostasis occurs, demonstrating the haemostasis function. A bleeding chamber is formed in the area surrounding the supported sample tubes 30 and 32. A supply of warm saline solution enters the base through a port 25 which is connected through the waste receptacle by an appropriate tubing conduit, and leaves port 68 which is inserted in the inlet 66. The inlet 66 and an overflow 65 keep the area defining a bleeding chamber continuously washed with warm saline solution. The overflow 65 conveys saline solution through a port 69 connected to the interior of the waste receptacle.

Drain tubes 63 and 64 collect blood which results from punching the holes through sample tubes 30 and 32. These collected drops of blood are washed with the saline solution through each of the drain tubes 63 and 64 into the waste receptacle 44 via openings 83. The drain tubes 63 and 64 are tapered to a narrow section entering the receptacle 44. The tapered portion is advantageously exposed to permit a photodetector to be inserted on each side of the drain tube narrow ends to sense the onset of bleeding and also the stopping of bleeding.

As was described in the foregoing earlier documents, i.e., the PCT international application, and EPO application, the pressure formed in the hydraulic circuit include the blood sample containers 12 and 14, as well as the blood collection chambers 40 and 42, may be monitored to measure the clotting characteristics of the blood. The pressure transducer is advantageously connected through the injection sites 45 and 47, which were previously precharged with the pressurized media. Thus, once the sample tubes have been punched, and bleeding commences, the pressure drop within these individual hydraulic circuits may be monitored to determine the forming of clotting within the punched holes.

The punching station 72 permits the accurate positioning of the punching needle 73 with respect to the sample tube 30 which is to be punctured. An alignment guide 74 and plunger guide 77 move in unison with the plunger 76, thus capturing the sample tube 30 Once so captured, and held rigidly within the larger opening of the drain tube 63, the needle 73 is forced against the needle spring 75 by continued forward movement of the plunger 76. The plunger 76 is held within the plunger guide 77 inserted in plunger housing 81 on the blood supply reservoir 11. Additional plunger springs 78 are maintained within the housing 81 by an assembly washer 79.

In operation, plunger buttons 84, not shown in FIG. 1, but described in the remaining Figures of the case, are forced upward by the spring 78. Manual pressure on each of the buttons will result in the spring 78 being compressed, and the plunger 76 and alignment guide 74 to be moved towards the drain tube 63. The alignment guide 74 will capture the sample tube 30 and cease moving forward along the axial direction of the drain tube 63. The needle 73 will continue to move against the force of needle spring 75, while the alignment guide 74 and plunger guide 77 are maintained stationary by the sample tube 30, supported within the drain tube opening 63. The alignment guide 74 insures that the drain tube is accurately punched across its diameter, and that the needle is withdrawn through the action of the needle spring 75, and expansion of the plunger spring 78, so that bleeding commences on both sides of the sample tube 30.

The punching station provides an identical punch for punching the sample tube 32 so as to provide the identical hole structure having the same diameter to simulate an identical bleeding condition with sample tube 30.

As was described in the aforesaid references, haemostasis may be measured with the monitoring of the pressure within the blood collection chamber 42. Additional detection of bleeding and the stopping of bleeding may be sensed with the photodetectors arranged around the narrow ends of drain tubes 63 and 64.

The cassette device illustrated in FIG. 1 provides total isolation of the tested blood, avoiding any possible contamination through infected blood which may have been drawn from a patient. As is described in these earlier patent references, the bleeding time is measured as a time requiring the pressure of the system to return to its prepunched condition. Given enough time, the tubes will be occluded due to a clot forming within each of the sample tubes 30 and 32. This event may be noted as well when the pressure monitored in the respective blood collection chambers 40 and 42 decreases to zero, indicating an occluded tube. These various measurements are detailed in the previous patent references, and give researchers valuable information as to the haemostasis and thrombolysis activity of the blood.

A third chamber 41 collects blood forced from the blood sample container 13. As was described in the earlier-noted references, it may be important to do a test without simulating bleeding, but rather providing a collagen-induced thrombus formation with a sample of blood. By inserting a small piece of catgut or other collagen material within a sample tube 31, and monitoring the pressure on the associated blood collection chamber 41, it is possible to provide a time indication of the formation of a collagen-induced thrombus.

The provision of two blood sample containers 12 and 14 which are connected via blood sample tubes 30 and 32 to punching chambers, permits the measurement of thrombolysis-inducing and other agents to be made. One of the blood sample containers may include a measure of such thrombolysis agents, such as t-PA, to determine the effects of the agent on the blood of an individual patient. Thus, the haemostasis bleeding time, clotting time and other related conditions may be determined independent of the non-heparinized blood sample.

In connection with this type of testing for the device, the overflow tube 53 is passed through a fork 54 before entering the waste receptacle 44. The overflow tube 53, in the region near the fork 54, and upstream therefrom, is enlarged with respect to the remaining portion of the overflow tube 53. A cylindrical member 57 slides along an axis coincident with the axis of the fork 54 to clamp the overflow tube 53 into a closed condition. This will effectively pressurize the sample tube 30, thus increasing pressure on any platelet plug formed in the hole punched in the sample tube 30, expelling the platelet, thereby increasing the speed of the test. The enlarged portion of the overflow tube 53 reduces the rise time of pressure buildup within the sample tube 30.

Each of the overflow tubes 50, 51 and 53 include a coil portion which provides resistance for material being forced from the blood collection chambers 40, 41 and 42, and are connected to discharge into waste receptacle 44. The coil portions permit establishment of a system pressure of 60 mm of mercury during testing.

Having thus given a description of the major components of the blood-holding cassette, reference will now be made to the individual subcomponents to describe their operation in greater detail.

Figure 2:
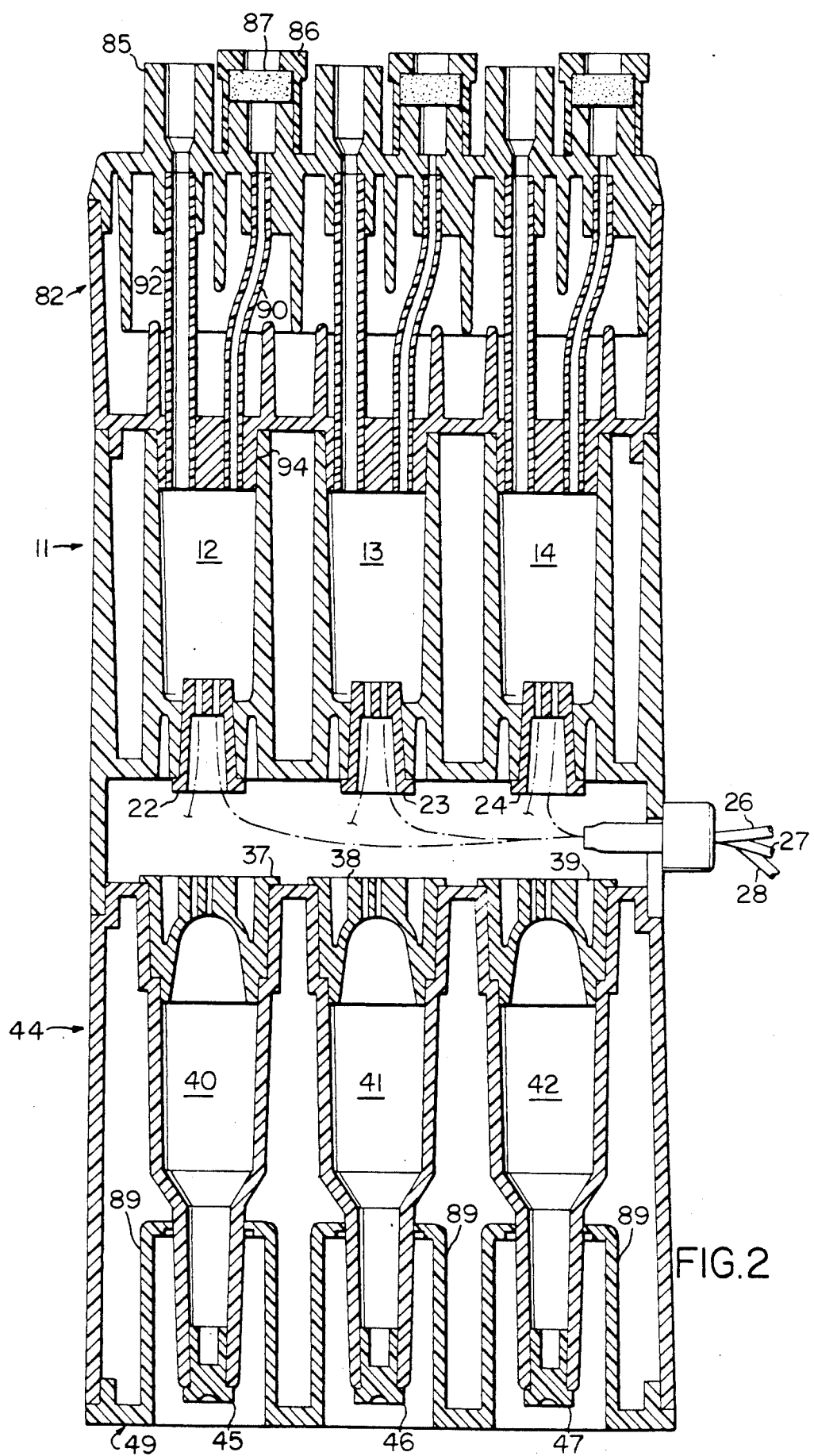
FIG. 2 is a section view of the blood sample container and blood collection chamber of the blood-holding cassette of FIG. 1.

FIG. 2 illustrates the relationship between the waste receptacle 44, the base 49, blood supply reservoir 11 and a previously undisclosed cap 82 which covers the blood supply reservoir 11, permitting each of the individual blood sample containers 12, 13 and 14 to be filled with a blood sample. The cap 82 includes for each blood sample container 12, 13 and 14 an inlet 85. When a blood sample is drawn, it may be readily injected into the blood sample container 12. The blood sample container 12 is sealed, using a pushbutton shown and described in FIGS. 3 and 4. A vent 86 includes a hydrophobic filter 87, permitting any air within the blood sample container 12 to vent through the filter 87.

Vents 86 and inlet 85 are connected via a sealing member 94 to the container 12. Individual flexible conduits 90 and 92 make the required connection between inlet and vents and the blood sample container 12.

It is clear that blood sample containers 13 and 14 contain identical structure for permitting the blood samples to be inserted in the individual blood sample containers will not be described further.

The blood sample container 11 is connected to the waste receptacle 44. In practice, each of the sections 82, 11, 44 and 49 are connected together with an adhesive, or otherwise made fluid-tight. The waste receptacle 44 includes an area between each of the collection chambers 40, 41 and 42 which collects saline and waste blood from drain tubes 63 and 64, and paraffin oil from overflow tubes 50, 51 and 53. The bottoms of the collection chambers 40, 41 and 42 are supported in supports 89 and are accessible via the injection sites 45, 46 and 47. These injection sites similarly are self-sealing, permitting pressurizing media to be injected within the blood collection chambers 40, 41 and 42, simultaneously permitting a pressure transducer to be connected to the same injection sites 45, 46 or 47. Obviously, a T-tube external to the injection sites 45, 46 and 47 will permit pressurizing media to be introduced, as well as permit pressure measurements to be monitored following the pressurizing of blood collection chambers 40, 41 and 42.

Figure 3:
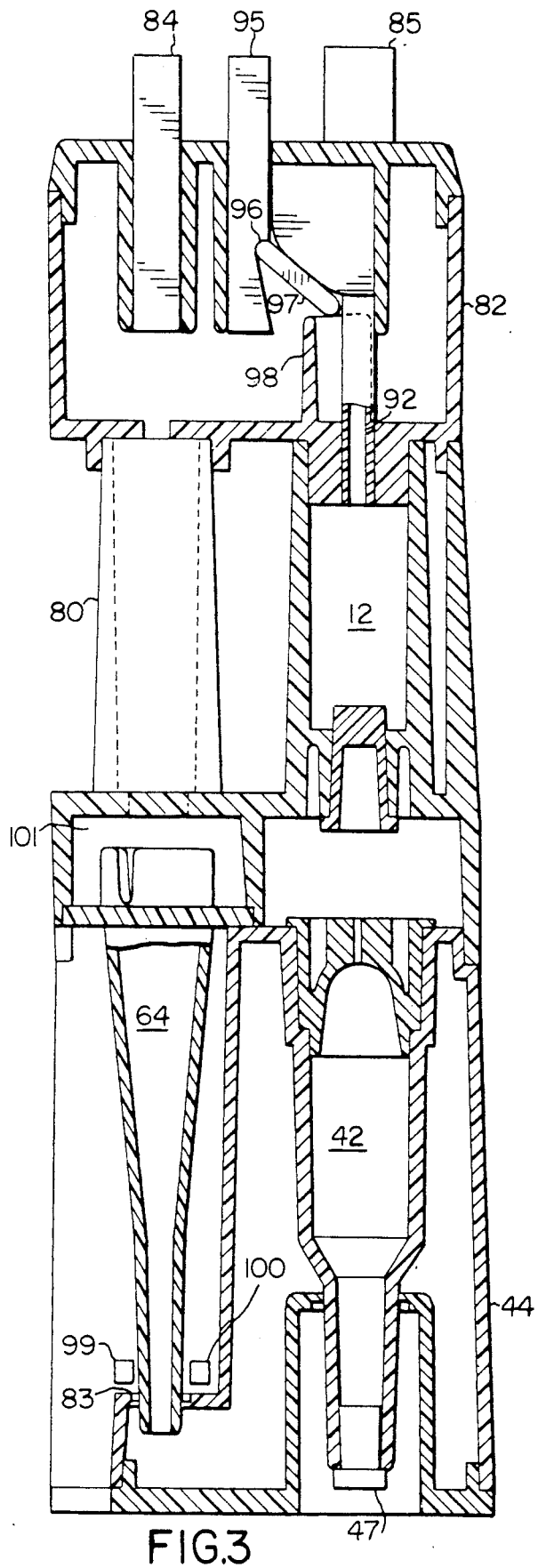
FIG. 3 illustrates yet another section view of the blood-holding cassette of FIG. 1, illustrating the relationship of the punching station and bleeding chamber with respect to the blood sample container and blood collection chamber.
Figure 4:
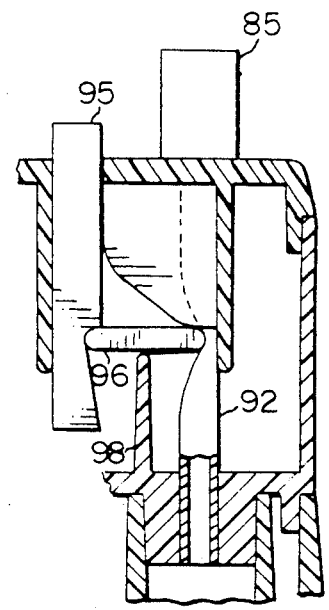
FIG. 4 illustrates the controls provided to seal the inlet and vent of the individual containers of the blood reservoir.

Referring now to FIG. 3, there is shown another section view of the blood sample cassette, illustrating various pushbuttons which are provided in the cap 82 of FIG. 2 for sealing each of the tubes 90 and 92, once the blood sample has been inserted in the blood chamber. FIG. 3 demonstrates one of three pushbuttons 95 held in a channel of the cap 82. At one end of the pushbutton 95 is an arcuate notch 96 which engages a lever 97. The lever 97 is supported to be cantilevered about an upstanding vertical rib 98 within the cap 82. As FIG. 4 demonstrates, when the button 95 is pressed downward, the lever 96 pivots about the upstanding vertical pivot 98, crimping the tube 92 and adjacent tube 90, connected to the inlet. In operation, once each of the sample containers 12, 13 and 14 are filled, they are sealed off by depressing the respective button 95 associated with the chamber 12. There are additional shut-off structures for blood sample containers 13 and 14, identical to that illustrated for chamber 12. In operation, as the cassette is designed to be thrown out once a test is made, the buttons 95 remain in their depressed position, closing off the vent and inlet of the blood sample container 12.

FIG. 3 also illustrates how a bleeding chamber 101 is formed, in a platform on the blood supply reservoir 11. The chamber includes the wider end of the drain tubes 63, 64, which positions blood sample tubes for puncture with respect to the plunger supports 80, 81. A pair of buttons 84 are located above plunger supports 80, 81 for moving a plunger into punching position. At the bottom of the drain tube 64 there is shown a space in which a photodetector 100 and light source 99 may be inserted to facilitate detection of blood dripping in the drain tube 64.

The aperture 83 receives the narrow end of the drain tube 64. The waste receptacle 44 is shown to have a space between the blood collection chambers 40, 41 and 42 to receive the blood and saline which drains through the tube 64.

Figure 5:
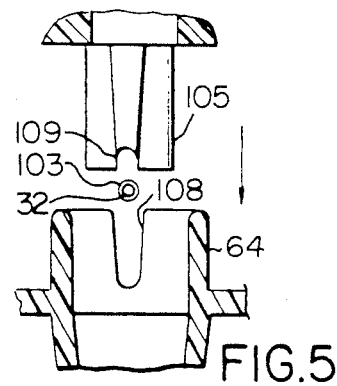
FIG. 5 shows the arrangement for holding the blood sample tube in the bleeding chamber of the device.
Figure 6:
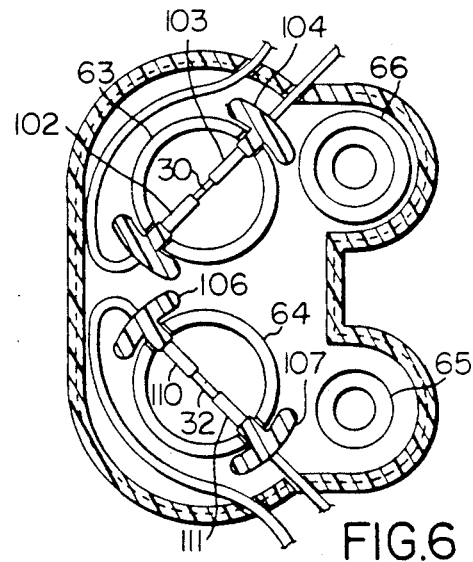
FIG. 6 is a top view of the bleeding chamber of the device positioning the blood sample tubes in the punching station.

FIGS. 5 and 6 illustrate in greater detail the blood chamber 101. The top of the drain tubes 63 and 64 have notches 108 diametrically opposite each other. The notches 108 receive tube clamps 104, 105, 106 and 107. These devices accurately position each of the sample tubes 30 and 32 to extend across the diameter of the drain tubes 63 and 64. The tube clamps 104, 105, 106 and 107 are inserted in each of the notches 108 of the drain tube to maintain the sample tubes 30 and 32 across the diameter of the drain tube 64. Extending from the tube clamps 104, 105, 106 and 107 toward the center of the drain tubes are metal support tubes 102, 103, 110, 111, slid over blood tubes 30, 32, which rigidly support the blood tubes 30, 32, exposing the center of the drain tubes 63, 64. Deflection of the tubes 30, 32 is held to a minimum during punching.

The bleeding chamber 101 is positioned with respect to the plunger guides 80, 81 so as to permit accurate location of the sample tube 30 and 32 with respect to an alignment guide contained on the plunger. The saline enters through port 66 at a very low rate, and exits the overflow 65 to wash any blood which results from simulated bleeding flowing through the drain tube 64 into the waste receptacle 44.

Figure 7:
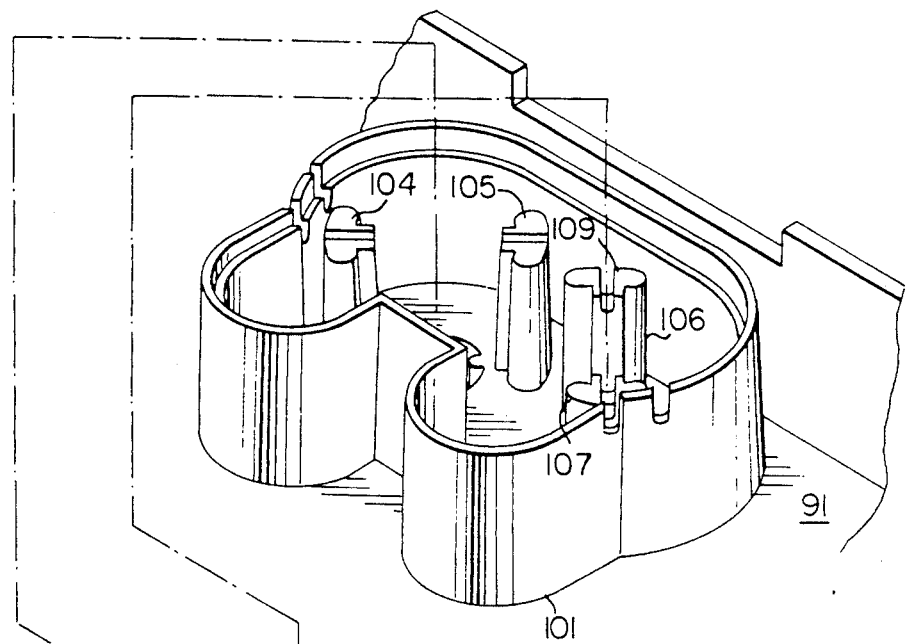
FIG. 7 is a perspective view of the bleeding chamber positioned underneath the punching station.
Figure 8:
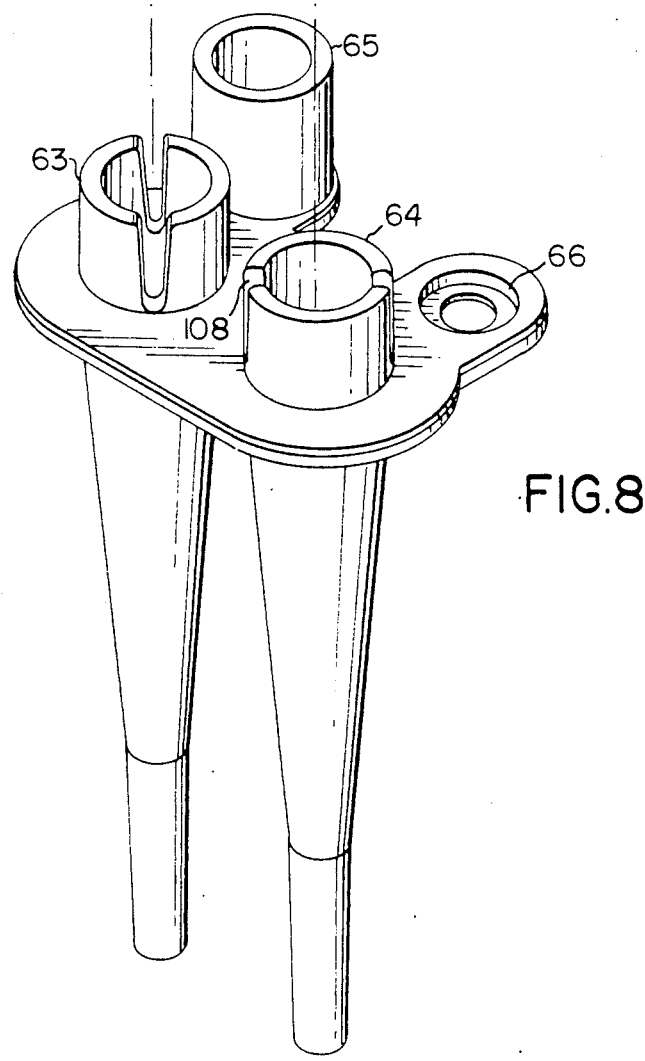
FIG. 8 illustrates the drain tube portion of the punching station as it relates to the bleeding chamber.

FIGS. 7 and 8 illustrate perspective views of the bleeding chamber 101 which is formed in the platform 91 of the blood supply reservoir 11. The tubes are first inserted through the notches 109 in the tube clamps 103, 104, 105 and 106, and then the drain tubes 63 and 64 are positioned to receive the clamping elements 103, 104, 105 and 106. The saline inlets and outlets 65 and 66 are positioned in similar openings of the bleeding chamber 101.

Thus, it is seen that the sample tubes to be punctured are parallel to the horizontally extending platform 91 of the reservoir.

FIGS. 9 through 11 illustrate how the plunger 72 accurately pierces a hole across the diameter of the sample tube 32. A pushbutton 84 is connected to the end of plunger 76. The plunger 76 shaft extends through the cap 82 and supports at an opposite end a needle 73. A plunger spring 78 is captured and maintained fixed between assembly washer 79 fixed to the plunger 76 shaft, and the plane 77c of a plurality of vertical ribs 77b of the plunger housing 80. The plunger 76 and plunger guide 77 will move until the alignment guide 74, connected to plunger guide 77, is seated against the blood sample tube 32. Continued movement of the plunger 76 will force needle 73 to move against its bias spring 75, punching the sample tube which is seated within the guide 74. Once the pushbutton 84 has been pushed its full limit and released, the plunger spring 78 will return the plunger 76 to its prepunched position. The needle spring 75 will additionally retract the punching needle along the punching axis within the alignment guide 74 to its prepunched position.

It is therefore seen that the punch within the punching station shown in FIG. 9 can accurately punch a sample tube along its major diameter. In order to compare successive testing of blood samples over a period of time, it is necessary to punch the same diameter hole and simulate bleeding under the same conditions in order to compare data obtained during each test. The diameter of the hole punched must be repeatable in a size range of 100-200 microns, and the needle must pierce the tubing with the full diameter of the needle shank. The foregoing device will maintain the blood sample tube fixed to permit diametrical piercing of the sample tube, and avoid any deflection which would result in a non-uniform piercing of the sample tube.

Thus, the foregoing device will provide for accurate punching of a blood sample tube having a wall thickness of less than 300 microns. This will accurately simulate the bleeding which occurs in small blood vessels which are physiologically related. The in vitro testing provided by this device will give accurate results of the physical environment experienced in human bleeding conditions.

An exploded view of the punching mechanism 72 is shown in FIG. 10. The assembly washer 79 retains one end of the plunger spring 78 within the plunger housing 80 fixed to the shaft of plunger 76. A pushbutton 84 rests on the end of the plunger shaft 76. The washer 79 moves with the plunger shaft 76 compressing plunger spring 78. When plunger shaft 76 moves downward against needle spring 75, the plunger guide is urged downward by the end of needle spring 75.

As the plunger guide 77 and plunger shaft 76 move into punching position, the alignment guide 74 connected to plunger guide 77 will capture the sample blood tube 32. As the sample blood tube 32 is fixed in its position by the clamp elements within the bleeding chamber 101, the alignment guide 74 and plunger guide 77 cease axial movement as the alignment guide 74 bottoms out on the blood sample tube 32. The plunger 76 supporting at one end thereof the piercing needle 73, continues to move within the plunger guide 77 against the needle spring 75. A shoulder 76a captures a needle spring 75 with the plunger guide 77. The plunger 76 and needle 73 are free to move axially with respect to the plunger guide 77 when it bottoms out due to the capture of the blood sample tube. The alignment guide 74 comprises two halves, one half having a slot for permitting movement of the needle within the alignment guide. One of the vertical ribs 77b is used to position the plunger guide 77 to move only in an axial direction within the plunger housing 80. Thus, upon depression of the plunger button 84, the guide 77 moves axially along the plunger housing 80 until the alignment guide 74 bottoms out about the blood sample tube. At this point, the plunger button 84 continues to advance the plunger 76 against the needle spring 75, puncturing the captured blood sample tube.

FIG. 11 illustrates a section view of the plunger device, showing plunger guide 77 guided by one of the vertical ribs 77b within the plunger housing 80.

Thus, it is clear that the foregoing device will provide for accurate and repeatable in vitro haemostasis testing of freshly drawn blood. The device can be used, using the principles set forth in the earlier patent literature referred to herein, to measure haemostasis and the effects of agents on the haemostasis thrombolytic properties of blood. Those skilled in the art will recognize yet other embodiments of the invention defined more particularly by the claims which follow.

What is claimed is:

1. A device for measuring haemostasis properties of a blood sample comprising:
   a blood sample reservoir for receiving a blood sample through an inlet, and for receiving a displacing material forcing said blood sample through an outlet;
   a blood sample tube connected to said outlet and connected to a collection chamber for receiving displaced blood; and,
   a punching station located along said blood sample tube for punching a hole in said tube, whereby blood exits said hole, simulating bleeding, said punching station including a drain tube having a top end centered with respect to said hole collecting said exiting blood, said drain tube being tapered from said top end to a narrower discharge end connected to a compartment of said collection chamber, said narrow end permitting detection of blood droplets formed from said simulated bleeding.

2. The device of claim 1 wherein said drain tube includes means for supporting said blood sample tube in alignment with an axis of said drain tube.

3. The device of claim 1 wherein said punching station comprises:
   a plunger supported for movement along an axis of said drain tube against a biasing spring; an alignment guide for centering said blood sample tube when said plunger is forced against said biasing spring; and,
   a punching needle centrally located with respect to said alignment guide, said punching needle forming a precisely aligned hole in said centered tube when said plunger is forced against said biasing spring.

4. The device of claim 3 wherein said punching needle is supported for axial movement with respect to said alignment guide.

5. The device of claim 3 wherein said punching needle is supported for axial movement with said plunger against a second biasing spring, and pushbutton means for moving said alignment guide into centering relation with said tube, and further moving said punching needle into said blood sample tube, whereby said needle accurately punches said blood tube, and said second bias spring extracts said needle from said blood sample tube when said pushbutton is released.

6. The device of claim 1 further comprising a supply of saline connected to said drain tube for continuously washing blood droplets from said drain tube.

7. A disposable blood cassette for a haemostasis measuring device comprising:
   a plurality of blood sample containers supported in a saline solution jacket, said blood sample containers having a sealable inlet and vents permitting individual blood samples to be introduced, and each having a paraffin oil supply line for forcing blood through a respective outlet;
   a blood waste receptacle fixed to said blood sample containers having a plurality of chambers connected to said outlets via individual blood sample tubes; and,
   a blood sample tube punching station supported on an exterior of said surface of said blood waste receptacle including at least one tapered drain tube having one end traversed by one of said blood sample tubes, and the remaining end connected to a compartment in said waste receptacle, said punching station including a punching means for punching a hole in said blood sample tube, whereby blood droplets form in said drain tube providing a detectable indication of bleeding.

8. The disposable blood haemostasis measuring device of claim 7 wherein said drain tube is connected at one end to a supply of saline for removing blood droplets in said drain tube.

9. The disposable blood haemostasis measuring device of claim 7 further comprising an inlet and outlet member for detachably connecting a source of saline solution to said saline solution jacket.

10. The disposable blood haemostasis measuring device of claim 7 wherein said blood waste receptacle comprises at least one pressurized collection chamber connected to said one blood sample tube, and adapted to be connected to a source of pressurizing media, and to a pressure transducer which senses a change in pressure in said blood sample tube resulting from clotting of a hole punched in said blood sample tube.

11. The disposable blood haemostasis measuring device of claim 10 further comprising a base connected to said blood waste receptacle connecting said pressurized collection reservoir to said source of pressurizing media and to said pressure transducer.

12. A disposable blood holding cassette for a haemostasis measuring device comprising:
   a blood sample reservoir having three separate pressurized blood sample containers, said blood sample reservoirs being surrounded by a liquid-tight jacket which receives a recirculated heating media;
   a waste blood collection reservoir having three separate pressurized chambers supported on a base, and a separate compartment in said base having first and second openings for storing waste blood;
   first, second and third blood sample tubes connecting each of said blood sample containers with a respective pressurized chamber, permitting flow of blood from said blood sample reservoirs to each pressurized chamber; and,
   a punching station comprising first and second drain tubes having an open end traversed by said first and second sample tubes, and having a second end connected to said first and second openings of said compartment, and first and second punching plungers which accurately locate first and second punching needles with respect to said traversing portions of said sample tubes, and subsequently puncture said traversing portions with said needles simulating bleeding, droplets of blood flowing towards said second ends of said drain tubes into said base.

13. The disposable haemostasis measuring device of claim 12 comprising a saline solution inlet on said base connected to an inlet on said first and second drain tubes for supplying a quantity of saline solution for removing blood droplets from said drain tubes.

14. The disposable haemostasis measuring device of claim 12 further comprising first, second and third pressurizing inlets on said base for supplying pressurizing media to said pressurized chambers.

15. The disposable haemostasis measuring device of claim 12 wherein said base includes first and second inlets connected to first and second recirculation inlets on said liquid-tight jacket.

16. The disposable haemostasis measuring device of claim 12 wherein one of said pressurized chambers, includes an overflow tube connected to said base waste compartment.

17. The disposable haemostasis device of claim 16 further comprising a clamp for shutting off said overflow tube, thereby increasing fluid pressure in said one pressurized chamber and a connected blood sample tube breaking down any clot forming in a puncture formed in said blood tube.

18. The disposable haemostasis device of claim 17, wherein said overflow tube has at an end upstream from said clamp an enlarged diameter for reducing the rate of increase in pressure which results from said clamp.

* * * * *